US012396661B2

(12) United States Patent
Sonner et al.

(10) Patent No.: US 12,396,661 B2
(45) Date of Patent: *Aug. 26, 2025

(54) DEVICES FOR INTEGRATED INDIRECT SWEAT STIMULATION AND SENSING

(71) Applicant: University of Cincinnati, Cincinnati, OH (US)

(72) Inventors: Zachary Cole Sonner, Elsmere, KY (US); Jason C. Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 697 days.

This patent is subject to a terminal disclaimer.

(21) Appl. No.: 16/597,169

(22) Filed: Oct. 9, 2019

(65) Prior Publication Data

US 2020/0037937 A1 Feb. 6, 2020

Related U.S. Application Data

(63) Continuation of application No. 15/544,725, filed as application No. PCT/US2016/017726 on Feb. 12, 2016, now Pat. No. 10,485,460.

(Continued)

(51) Int. Cl.
*A61B 5/145* (2006.01)
*A61B 5/00* (2006.01)
(Continued)

(52) U.S. Cl.
CPC ........ *A61B 5/14521* (2013.01); *A61B 5/0533* (2013.01); *A61B 5/14507* (2013.01);
(Continued)

(58) Field of Classification Search
CPC .............. A61B 5/14521; A61B 5/14517
(Continued)

(56) References Cited

U.S. PATENT DOCUMENTS 4,190,060 A 2/1980 Greenleaf et al.
4,542,751 A 9/1985 Webster et al.
(Continued)

FOREIGN PATENT DOCUMENTS

CA 2869469 A1 10/2013
CN 1874720 A 12/2006
(Continued)

OTHER PUBLICATIONS

Riedl et al., Spatial extension of sudomotor axon reflex sweating in human skin, Journal of the Autonomic Nervous System, 69 (1998) pp. 83-88 (Year: 1998).*

(Continued)

*Primary Examiner* — Puya Agahi
(74) *Attorney, Agent, or Firm* — Wood Herron & Evans LLP

(57) ABSTRACT

A sweat sensing device (20) comprises at least one sweat generation unit (22) capable of initiating sudomotor axon reflex (SAR) sweating in an indirect stimulation region and at least one analysis unit (24, 26) capable of sensing a physiological parameter of sweat, collecting a sweat sample, or a combination thereof. The at least one analysis unit (24, 26) is located above the indirect stimulation region when the sweat sensing device is placed on skin.

13 Claims, 6 Drawing Sheets

Related U.S. Application Data

(60) Provisional application No. 62/115,851, filed on Feb. 13, 2015.

(51) Int. Cl.
*A61B 5/053* (2021.01)
*A61B 5/0533* (2021.01)
*A61B 10/00* (2006.01)
*A61N 1/04* (2006.01)
*A61N 1/32* (2006.01)

(52) U.S. Cl.
CPC ........ *A61B 5/14517* (2013.01); *A61B 5/4266* (2013.01); *A61B 10/0064* (2013.01); *A61B 5/053* (2013.01); *A61B 2560/0412* (2013.01); *A61B 2562/166* (2013.01); *A61N 1/0428* (2013.01); *A61N 1/325* (2013.01)

(58) Field of Classification Search
USPC .................................................. 600/307, 346
See application file for complete search history.

(56) References Cited

U.S. PATENT DOCUMENTS

| | | | |
|---|---|---|---|
| 4,756,314 A | 7/1988 | Eckenhoff et al. | |
| 4,820,263 A | 4/1989 | Spevak et al. | |
| 5,036,861 A * | 8/1991 | Sembrowich | A61N 1/325 604/20 |
| 5,050,604 A | 9/1991 | Reshef et al. | |
| 5,140,985 A | 8/1992 | Schroeder et al. | |
| 5,246,003 A | 9/1993 | DeLonzor | |
| 5,438,984 A | 8/1995 | Schoendorfer | |
| 5,480,651 A | 1/1996 | Callaway | |
| 5,556,789 A | 9/1996 | Goerlach-Graw et al. | |
| 5,814,599 A | 9/1998 | Mitragotri et al. | |
| 5,944,662 A | 8/1999 | Schoendorfer | |
| 6,132,975 A | 10/2000 | Kanan et al. | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0193030 A1* | 9/2004 | Aston | A61B 10/0064 600/362 |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0096520 A1 | 5/2005 | Maekawa et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1* | 2/2007 | Peyser | G01N 33/66 600/362 |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0179403 A1 | 7/2010 | Martinsen et al. | |
| 2010/0198521 A1 | 8/2010 | Haick | |
| 2010/0234712 A1 | 9/2010 | Sugenoya et al. | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0271125 A1 | 10/2012 | Bernstein et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0053817 A1 | 2/2013 | Yun | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0197333 A1 | 8/2013 | Petisce | |
| 2013/0245388 A1 | 9/2013 | Rafferty et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0066726 A1 | 3/2014 | Costello | |
| 2014/0163338 A1 | 6/2014 | Roesicke | |
| 2014/0206977 A1 | 7/2014 | Bahney et al. | |
| 2014/0257064 A1 | 9/2014 | Einck et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |
| 2016/0249847 A1* | 9/2016 | Kennedy | A61N 1/30 600/307 |

FOREIGN PATENT DOCUMENTS

| | | |
|---|---|---|
| CN | 1969184 A | 5/2007 |
| CN | 1984716 A | 6/2007 |
| CN | 101380240 A | 3/2009 |
| CN | 101489470 A | 7/2009 |

(56) References Cited

FOREIGN PATENT DOCUMENTS

| | | |
|---|---|---|
| CN | 201508360 U | 6/2010 |
| EP | 0282349 A2 | 9/1988 |
| EP | 0453283 A1 | 10/1991 |
| EP | 0634215 A1 | 1/1995 |
| EP | 0766578 B1 | 10/2000 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009019686 A2 | 2/2009 |
| WO | 2009052321 A2 | 4/2009 |
| WO | 2010017578 A1 | 2/2010 |
| WO | 2010045247 A1 | 4/2010 |
| WO | 2010075115 A2 | 7/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015120439 A1 | 8/2015 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |
| WO | 2017019573 A1 | 2/2017 |
| WO | 2017019602 A1 | 2/2017 |
| WO | 2017070640 A1 | 4/2017 |

OTHER PUBLICATIONS

International Searching Authority, Search Report and Written Opinion issued in International Application No. PCT/US2017/067495 mailed Mar. 1, 2018, 10 pages.
International Searching Authority/US, International Search Report and Written Opinion issued in corresponding PCT Application No. PCT/US2016/059392, mailed on Feb. 15, 2017 (12 pages).
European Patent Office, Extended Search Report issued in European Application No. 15844313.5 mailed on Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Supplementary European Search Report issued in corresponding European Application No. EP 16749949, dated Jun. 15, 2018 (7 pages).
European Patent Office, Extended European Search Report issued in European Application No. 16753129.2, dated Jun. 15, 2018 (8 pages).
European Patent Office, Extended European Search Report issued in European Application No. 15800539.7, dated Aug. 17, 2018 (6 pages).
Chinese Patent Office, English translation of Office Action issued in Chinese Application No. 201480067960.8, dated Dec. 11, 2018, 3 pages.
European Patent Office, extended European Search Report issued in European Patent Application No. 16831190.0, mailed on Jan. 30, 2019 (8 pages).
Song et al., Aptamer-based biosensors, Trac Trends in Analytical Chemistry, vol. 27, No. 2, Dec. 23, 2007, pp. 108-117.
European Supplementary Search Report in European Patent Application No. 16845111, dated Mar. 14, 2019, 9 pgs.
European Supplementary Search Report in European Patent Application No. EP 16860910.5, received Jun. 4, 2019, 4 pgs.
Chinese Patent Office, English translation of Office Action issued in corresponding Chinese Application No. 201480067960.8, dated Dec. 11, 2018, 3 pages.
European Patent Office, Extended European Search Report issued in corresponding European Application No. 15800539.7, dated Aug. 17, 2018 (6 pages).
European Patent Office, Extended European Search Report issued in corresponding European Application No. 16753129.2, dated Jun. 15, 2018 (8 pages).
European Patent Office, extended European Search Report issued in corresponding European Patent Application No. 16831190.0, mailed on Jan. 30, 2019 (8 pages).
European Search Report in European Patent Application No. 19173145.4, received Jul. 30, 2019, 5 pgs.
European Search Report in European Patent Application No. 19173149.6, received Aug. 23, 2019, 6 pgs.
European Search Report in European Patent Application No. 19173145.4, received Jul. 30, 2019, 6 pgs.
European Search Opinion in European Patent Application No. 16860910.5, dated Jun. 27, 2019, 4 pgs.
International Search Report and Written Opinion in International Patent Application No. PCT/US2017/047574, mailed Nov. 16, 2017, 14 pgs.
Office Action in U.S. Appl. No. 15/680,611, dated Jul. 25, 2019, 25 pgs.
Spencer, H.J. "Programmable nanoampere constant current sources for iontophoresis". Med. & biol. Engng. (1971) 9:693. https://doi.org/10.1007/BF02474650 <https://doi.org/10.1007/BF02474650> (Year: 1971).
Khurana, R.K. "Cholinergic dysfunction in Shy-Drager syndrome: Effect of the parasympathomimetic agent, bethanechol". Clinical Autonomic Research (1994) 4: 5. <https://doi.org/10.1007/BF01828832> (Year: 1994).
Shibasaki M, Crandall CG. "Effect of local acetylcholinesterase inhibition on sweat rate in humans". J Appl Physiol. (2001) 90(3): 757-762 (Year: 2001).
Lang, E. , Spitzer, A. , Claus, D. , Neundorfer, B. and Handwerker, H. 0. Abstract of "Stimulation of sudomotor axon reflex mechanism by carbachol in healthy subjects and patients suffering from diabetic polyneuropathy". Acta Neurologica Scandinavica, 1995) 91: 251-254. (Year: 1995).
European Search Report in European Patent Application No. 19188927.8, dated Oct. 23, 2019, 9 pgs.
Australian Patent Office, Notice of Acceptance for Patent Application issued in Australian Application No. 2013243541 on Mar. 23, 2017 (3 pages).
Chinese Patent Office, First Office Action issued in Chinese Application No. 201380028053.8 issued Dec. 21, 2015, 4 pages.
European Patent Office, Written Opinion of the International Searching Authority / International Preliminary Report on Patentability mailed Oct. 16, 2014 (14 pages).
Fu et al., "Controlled Reagent Transport in Disposable 2D Paper Networks", The Royal Society of Chemistry 2010, Lab Chip, 2010, 10, 918-920.
International Bureau, Notification Concerning Transmittal of International Preliminary Report on Patentability issued in International Application No. PCT/US13/35092 on Oct. 7, 2014, 14 pages.
International Searching Authority, Invitation to Pay Additional Fees and, Where Applicable, Protest Fee, and Communication Relating

(56) References Cited

OTHER PUBLICATIONS to the Results of the Partial International Search, issued in International Application No. PCT/US13/35092 mailed Aug. 26, 2013, 9 pages.
International Searching Authority, Invitation to Pay Additional Search Fees and, Where Applicable, Protest Fee, and Communication Relating to the Results of the Partial International Search, issued in corresponding International Application No. PCT/US2014/061083 dated Dec. 15, 2014, 6 pages.
International Searching Authority, Invitation to Pay Additional Search Fees and, Where Applicable, Protest Fee, and Communication Relating to the Results of the Partial International Search, issued in International Application No. PCT/US2015/032843 mailed Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 mailed Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 mailed Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 mailed Dec. 1, 2015, 2 pages.
International Searching Authority, Search Report and Written Opinion issued in International Application No. PCT/US2014/061098 mailed Dec. 19, 2014, 13 pages.
International Searching Authority, Search Report and Written Opinion issued in International Application No. PCT/US2015/032893 mailed Nov. 13, 2015, 14 pages.
International Searching Authority, Search Report and Written Opinion issued in International Application No. PCT/US2015/032866 mailed Nov. 19, 2015, 12 pages.
International Searching Authority, Search Report and Written Opinion issued in International Application No. PCT/US2015/051439 mailed Dec. 28, 2015, 7 pages.
International Searching Authority, Search Report and Written Opinion issued in International Application No. PCT/US2015/040113 mailed Feb. 4, 2016, 13 pages.
International Searching Authority, Search Report and Written Opinion issued in International Application No. PCT/US16/18635 mailed May 6, 2016, 12 pages.
International Searching Authority, Search Report and Written Opinion issued in International Application No. PCT/US16/17726 mailed May 12, 2016, 9 pages.
Stoppa, Matteo, et al., "Wearable Electronics and Smart Tectiles: A Critical Review," Sensors, 2014, pp. 11957-11992, vol. 14 (36 pages).
Basi, Thin-layer Cell Gaskets, https://www.basinc.com/products/ec/gaskets[Oct. 10, 2017 2:43:33 pm] (8 pages).
Mizuguchi, Hitoshi, et al., "A dual-electrode flow sensor fabricated using track-etched microporous membranes," Talanta, vol. 96, 2012, pp. 168-173, Elsevier (6 pages).
Mizuguchi, Hitoshi, et al., "A Triple-Electrode Based Dual-Biosensor System Utilizing Track-Etched Microporous Membrane Electrodes for the Silultaneous Determination of L-Lactate and D-Glucose," Bull. Chem. Co. Jpn., vol. 90, 2017, pp. 1211-1216, The Chemical Society of Japan (6 pages).
Argatroban Injection, Package Insert for Argatroban Injection, "Highlights of Prescribing Information," Research Triangle Park, NC, GlaxoSmithKline, 2012 (22 pages).
Balant-Gorgia, Androniki E., et al., "Clinical Pharmacokinetics of Clompipramine," Clin. Pharmacokinet., vol. 20(6), 1991, pp. 447-462 (16 pages).

Baxter, Roger, et al., "Comparison of Bactericidal Activity of Five Antibiotics against *Staphylococcus aureus*," Oxford Journals, The Journal of Infectious Diseases, vol. 161, No. 5, May 1990, pp. 1023-1025, Oxford University Press (4 pages).
Bertrand, Julie, et al., "Influence of pharmacogenetics on indinavir dispostion and short-term response in HIV patients initiating HAART," Eur J Clin Pharmacol., Jul. 22, 2010, vol. 65(7), pp. 667-678 (17 pages).
Bockbrader, Howard N., et al., "Clinical Pharmacokinetics of Pregabalin in Healthy Volunteers," Journal of Clinical Pharmacology, 2010, vol. 50, pp. 941-950 (10 pages).
Buch, A.B., et al., "A Study of Pharmacokinetic Interaction Between Buspirone and Alprazolam at Steady State," J Clin Pharmacol, 1993, vol. 33, pp. 1104-1109 (6 pages).
Fonseca, Walter, et al., "Comparing Pharmacokinetics of Amoxicillin Given Twice or Three Times per Day to Children Older than 3 Months with Pneumonia," Antimicrobial Agents and Chemotherapy, Mar. 2003, vol. 47, No. 3, pp. 997-1001, American Society for Microbiology (5 pages).
Friedrich, Lawrance V., et al., "Aztreonam Pharmacokinetics in Burn Patients," Antimicrobial Agents and Chemotherapy, Jan. 1991, vol. 35, No. 1, pp. 57-61, American Society for Microbiology (5 pages).
Garcia, David A., et al., "Parenteral Anticoagulants: Antithrombotic Therapy and Prevention of Thrombosis, 9th ed: American College of Chest Physicians Evidence-Based Clinical Practice Guidelines," Chest, 2012, vol. 141/2 (Supplement), pp. e24S-e43S (20 pages).
Geller, David E., et al., :Pharmacokinetics and Bioavailability of Aerosolized Tobramycin in Cystic Fibrosis, Chest, vol. 122, No. 1, Jul. 2002, pp. 219-226 (8 pages).
Glazer, William M., et al., "The determination of the steady-state pharmacokinetic profile of fluphenazine decanoate by gas chromatography/mass spectrometry detection," Schizophrenia Research, 1992, vol. 8, pp. 111-117, Elsevier Science Publishers B.V. (7 pages).
Goodwin, Megan L., et al., "Antifungal serum concentration monitoring: an update," Journal of Antimicrobial Chemotherapy, 2008, vol. 61, pp. 17-25, Advance Access publicaiton Nov. 12, 2007 (9 pages).
Hsu, Ann, et al., "Multiple-Dose Pharmacokinetics of Ritonavir in Human Immunodeficiency Virus-Infected Subjects," Antimicrobial Agents and Chemotherapy, May 1997, Vo. 41, No. 5, pp. 898-905, American Society for Microbiology (8 pages).
Hyland, R., et al., "Identification of the Cytochrome P450 Enzymes Involved in the N-Oxidation of Voriconazole," Drug Metabolism and Disposition, Jan. 2003, vol. 31, No. 5, pp. 540-547, The American Society for Pharmacology and Experimental Therapeutics (8 pages).
Kappelhoff, Bregt S., et al., "Pharmacokinetics of Nevirapine: Once-Daily Versus Twice-Daily Dosing in the 2NN Study," HIV Clinical Trials, Sep. 2005, vol. 6(5), pp. 254-261, Thomas Land Publishers, Inc. (9 pages).
La Porte, C.J.L., et al., "Pharmacokinetics of Adjusted-Dose Lopinavir-Ritonavir Combined with Rifampin in Healthy Volunteers," Antimicrobial Agents and Chemotherapy, May 2004, vol. 48, No. 5, pp. 1553-1560, American Society for Microbiology (8 pages).
Lacy, Melinda K., et al., "Comparison of bactericidal activity after multidose administration of clarithromycin, azithromycin, and cefuroxime axetil aginst *Streptococcus pneumoniae*," International Journal of Antimicrobial Agents 10, 1998, pp. 279-283, Elsevier (5 pages).
Lai, Allen A., et al., "Time-course of interaction between carbamazepine and clonazepam in normal man," Clin. Pharmacol. Ther., Sep. 1978, vol. 24, pp. 316-323, The C.V. Mosby Co. (8 pages).
Marshall, William F., et al., "The Cephalosporins," Symposium on Antimicrobial Agents—Part V, Mayo Clin Proc, 1999, vol. 74, pp. 187-195 (9 pages).
McIlleron, Helen, et al., "Determinants of Rifampin, Isoniazid, Pyrazinamide, and Ethambutol Pharmacokinetics in a Cohort of Tuberculosis Patients," Antimicrobial Agents and Chemotherapy, Apr. 2006, vol. 50, No. 4, pp. 1170-1177, American Society for Microbiology (8 pages).

(56) References Cited

OTHER PUBLICATIONS

Medscape, "Drug, OTCs and Herbals | Medscape Reference," http://www.reference.medscapte.com/drugs, Accessed Mar. 2013 and Apr. 3, 2017 (1 page).
Mimaki, Takashi, "Clinical Pharmacology and Therapeutic Drug Monitoring of Zonisamide," Therapeutic Drug Monitoring, Dec. 1998, vol. 20(6), pp. 593-597, Lippincott Williams & Wilkins, Inc. (9 pages).
Molina, J-M., et al., "Pharmacokinetics of emtricitabine, didanosine andefavirenz administered once-daily for the treatment of HIV-infected adults (Pharmacokinetic substudy of the ANRS 091 trial)," HIV Medicine (2004), vol. 5, pp. 99-104, 2004 British HIV Association (6 pages).
Morse, Gene D., et al., "Multiple-Dose Pharmacokinetics of Delavirdine Mesylate and Didanosine in HIV-Infected Patients," Clin Drug Invest, 2003, pp. 323-328, vol. 23 (5), Adis Data Information BV (6 pages).
Munne P. International Programme on Chemical Safety Poisons Information Monograph 181, "Pharmacology and Toxicology," Published Apr. 1990, available at: http://www.inchem.org/documents/pims/pharm/pim181.htm#PartTitle:7.%20%20PHARMACOLOGY%20AND%20TOXICOLOGY, Accessed Oct. 2, 2009, pp. 14-18 (5 pages).
Nauta, Ernst H., et al., "Dicloxacillin and cloxacillin: Pharmacokinetics in healthy and hemodialysis subjects," Clinical Pharmacology and Therapeutics, vol. 20, No. 1, Feb. 13, 1976, pp. 98-108 (11 pages).
Ochs, Hermann R., et al., "Digitoxin Accumulation," Br. J. clin. Pharmac. (1982), vol. 14, pp. 225-229. The Macmillan Press Ltd 1982 (5 pages).
Ordonez Gallego, A., et al., "Oxycodone: a pharmacological and clinical review," Clin Transl Oncol, 2007, vol. 9, pp. 298-307 (10 pages).
Pippenger, C.E., et al., "Principles of Therapeutic Drug Monitoring," In: Wong Shy, ed. Therapeutic Drug Monitoring and Toxicology by Liquid Chromatography. Boca Raton, FL: CRC Press, 1985, pp. 11-36 (26 pages).
Purkins, L., et al., "Pharmacokinetics and Safety of Voriconazole following Intravenous-to Oral-Dose Escalation Regimens," Antimicrobial Agents and Chemotherapy, Aug. 2002, vol. 46, No. 8, pp. 2546-2553, American Society for Microbiology (8 pages).
Purkins, Lynn, et al., "The pharmacokinetics and safety of intravenous voriconazole—a novel wide-spectrum antifungal agent," Br J Clin Pharmacol, 2003, vol. 56, pp. 2-9, Blackwell Publishing Ltd (8 pages).
Ratjen, F., et al., "Pharmacokinetics of inhaled colistin in patients with cystic fibrosis," Journal of Antimicrobial Chemotherapy, 2006, vol. 57, pp. 306-311 (6 pages).
Remmel, Rory P., et al., "Simultaneous Assay of Felbamate plus Carbamazepine, Phenytoin, and Their Metabolites by Liquid Chromatography with Mobile Phase Optimization," Therapeutic Drug Monitoring, 1990, vol. 12, pp. 90-96, Raven Press, Ltd., New York (7 pages).
Rosenfeld, W.E., et al., "Comparison of the Steady-State Pharmacokinetics of Topiramate and Valproate in Patients with Epilepsy During Monotherapy and Concomitant Therapy," Epilepsia, 1997, vol. 38(3), pp. 324-333, Lippincott-Raven Publishers, Philadelphia (10 pages).
Ruslami, Rovina, et al., "Pharmacokinetics and Tolerability of a Higher Rifampin Dose versus the Standard Dose in Pulmonary Tuberculosis Patients," Antimicrobial Agents and Chemotherapy, Jul. 2007, vol. 51, No. 7, pp. 2546-2551, American Society for Microbiology (6 pages).
Rythmol, Package Insert for Rythmol, "Highlights of Prescribing Information," Reliant Pharmaceuticals Inc., 2004 (24 pages).
Sadler, Brian M., et al., "Pharmacokinetic and Pharmacodynamic Study of the Human Immunodeficiency Virus Protease Inhibitor Amprenavir after Multiple Oral Dosing," Antimicrobial Agents and Chemotherapy, Jan. 2001, vol. 45, No. 1, pp. 30-37, American Society for Microbiology (8 pages).
Silverstein, Jeffrey H., et al., "An Analysis of the Duration of Fentanyl and Its Metabolites in Urine and Saliva," Anesth Analg, 1993, vol. 76:6, pp. 618-621, The International Anesthesia Research Society (4 pages).
Sobue, Satoshi, et al., "Pharmacokinetics of fosfluconzaole and fluconazole following multiple intravenous administration of fosfluconazole in healthy male volunteers," British Journal of Clinical Pharmacology, 2004, vol. 58:1, pp. 20-25, Blackwell Publishing Ltd. (6 pages).
Ti, Teow-Yee, et al., "Disposition of Intravenous Metronidazole in Asian Surgical Patients," Antimicrobial Agents and Chemotherapy, Oct. 1996, vol. 40, No. 10, pp. 2248-2251, American Society for Microbiology (4 pages).
Viracept, Package Insert for Viracept, "Highlights of Prescribing Information," Agouron Pharmaceuticals, 2008 (27 pages).
Von Hentig, Nils, et al., "Pharmacokinetics of Saquinavir, Atazanavir, and Ritonavir in a Twice-Daily Boosted Double-Protease Inhibitor Regimen," Antimicrobial Agents and Chemotherapy, Apr. 2007, vol. 51, No. 4, pp. 1431-1439, American Society for Microbiology (9 pages).
Wilens, Timothy E., et al., "Fluoxetine Pharmacokinetics in Pediatric Patients," Journal of Clinical Psychopharmacology, 2002, vol. 22, No. 6, pp. 568-575, Lippincott Williams & Wilkins, Inc. (8 pages).
Wong, Steven H.Y., "Therapeutic Drug Monitoring and Toxicology by Liquid Chromatography," Chromatographic Science Series, 1985, vol. 32, Chapter 2 "Principles of Therapeutic Drug Monitoring" by C.E. Pippenger, Marcel Dekker, Inc., New York and Basel (34 pages).
Yamamoto, Takatsugu, et al., "Pharmacokinetic Characteristics of Minocycline in Debilitated Elderly Patients," American Journal of Therapeutics, 1999, vol. 6, pp. 157-160 (4 pages).
Zyprexa Relprevv, Package Insert for Zyprexa Relprevv, "Highlights of Prescribing Information," Eli Lilly and Company, 2008 (27 pages).
International Bureau, Notification Concerning Transmittal of International Preliminary Report on Patentability issued in International Application No. PCT/US13/35092, 14 pages.
International Searching Authority, Invitation to Pay Additional Fees and, Where Applicable, Protest Fee, and Communication Relating to the Results of the Partial International Search, issued in International Application No. PCT/US13/35092, 9 pages.
European Patent Office, Official Communication for EP Application No. 13 718 933.8-1101 mailed Feb. 14, 2018 (5 pages).
European Patent Office, Extended European Search Report issued in European Application No. 15819306.0-1115 on Feb. 9, 2018 (9 pages).
International Searching Authority, Search Report and Written Opinion issued in corresponding International Application No. PCT/US2014/061098 issued Dec. 12, 2014, 13 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Search Report and Written Opinion issued in International Application No. PCT/US2014/061083 mailed Mar. 31, 2015, 18 pages.
International Searching Authority, Search Report and Written Opinion issued in International Application No. PCT/US2015/032830 mailed Aug. 14, 2015, 9 pages.
International Searching Authority, Search Report and Written Opinion issued in International Application No. PCT/US2015/032843 mailed Oct. 26, 2015, 11 pages.
International Searching Authority, Search Report and Written Opinion issued in International Application No. PCT/US2015/032866 issued Nov. 19, 2015, 12 pages.
International Searching Authority, Search Report and Written Opinion issued in International Application No. PCT/US2015/032893 issued Nov. 13, 2015, 14 pages.
International Searching Authority, Search Report and Written Opinion issued in International Application No. PCT/US2015/040113 issued Feb. 4, 2016, 13 pages.

(56) References Cited

OTHER PUBLICATIONS

International Searching Authority, Search Report and Written Opinion issued in International Application No. PCT/US2015/051439 issued Dec. 28, 2015, 7 pages.
International Bureau, Notification Concerning Transmittal of International Preliminary Report on Patentability issued in International Application No. PCT/US13/35092 mailed Oct. 16, 2014, 14 pages.
European Patent Office, Written Opinion of the International Search Authority / International Preliminary Report on Patentability for PCT/US2013/035092 mailed Oct. 16, 2014 (14 pages).
Australian Patent Office, Patent Examination Report No. 1 issued in Australian Application No. 2013243541 on Nov. 25, 2016, 4 pages.
European Patent Office, Partial European Search Report issued in European Application No. 16203346.8-1657 on Mar. 24, 2017, 7 pages.
International Searching Authority, Search Report and Written Opinion issued in International Application No. PCT/US16/59392 mailed Oct. 28, 2016, 13 pages.
International Searching Authority, Search Report and Written Opinion issued in International Application No. PCT/US16/50928 mailed Sep. 9, 2016, 8 pages.
Japanese Patent Office, Office Action issued in Japanese Application No. 2015-504702 issued Jan. 20, 2017, 7 pages (including English language translation).
Stoppa, Matteo, et al., "Wearable Electronics and Smart Textiles: A Critical Review," Sensors, 2014, pp. 11957-11992, vol. 14 (36 pages).
International Searching Authority, Search Report and Written Opinion issued in International Application No. PCT/US16/43862 mailed Oct. 19, 2016, 14 pages.
International Searching Authority, Search Report and Written Opinion issued in International Application No. PCT/US2017/013453 mailed May 18, 2017, 14 pages.
International Searching Authority, Search Report and Written Opinion issued in International Application No. PCT/US2017/039421 mailed Sep. 6, 2017, 10 pages.
International Searching Authority, Search Report and Written Opinion issued in International Application No. PCT/US2017/040588 mailed Sep. 25, 2017, 11 pages.
Chinese Patent Office, First Office Action issued in Chinese Application No. 201380028053.8 issued Dec. 21, 2105, 4 pages.
Australian Patent Office, Notice of Acceptance for Patent Applicatin issued in Australian Application No. 2013243541 on Mar. 23, 2017 (3 pages).
Chinese Patent Office, Second Office Action issued in Chinese Application No. 201380028053.8 issued Sep. 20, 2016, 8 pages (including English language translation).
Chinese Patent Office, Third Office Action issued in Chinese Application No. 201380028053.8 issued Mar. 20, 2017, 17 pages (including English language translation).
European Patent Office, Supplemental European Search Report issued in European Application No. 15799514.3-1657 on Dec. 7, 2017, 8 pages.
European Patent Office, Supplemental European Search Report issued in European Application No. 15799317.1-1657 on Dec. 21, 2017, 9 pages.
European Patent Office, Partial European Search Report issued in European Application No. 15800043.0-115 on Jan. 8, 2018, 13 pages.
International Searching Authority, Search Report and Written Opinion issued in International Application No. PCT/US2017/047574 issued Nov. 16, 2017, 14 pages.
International Searching Authority, Search Report and Written Opinion issued in International Application No. PCT/US2017/052651 issued Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.
International Searching Authority, Search Report and Written Opinion in International Application No. PCT/US2016/043862, mailed Oct. 19, 2016 (14 pages).
European Patent Office, Extended Search Report issued for European Application No. 15800043.0-1115 mailed Apr. 16, 2018, 11 pages.
Agwuh, Kenneth N., et al., "Pharmacokinetics and pharmacodynamics of the tetracyclines including glycylcyclines," Journal of Antimicrobial Chemotherapy, 2006, vol. 58, pp. 256-265, Advance Access Publication (10 pages).
Paixao, Thiago Regis Longo Cesar, et al., "The use of a new twin-electrode thin-layer cell to the study of homogeneous processes coupled to electrode reactions," Journal of Electroanalytical Chemistry, vol. 596, 2006, pp. 101-108, Elsevier (8 pages).
Office Action in U.S. Appl. No. 15/314,410, dated Jul. 9, 2019, 6 pgs.
European Official Letter in European Patent Application No. 16749949.0, dated Jul. 9, 2024, 6 pgs.

\* cited by examiner

DEVICES FOR INTEGRATED INDIRECT SWEAT STIMULATION AND SENSING

CROSS-REFERENCE TO RELATED APPLICATIONS

This application claims priority to and the benefit of the filing date of U.S. Patent Application Publication No. 2018/0035928 A1 (U.S. patent application Ser. No. 15/544,725), filed on Jul. 19, 2017, which is the U.S. national phase of International Patent Application No. PCT/US2016/017726 (International Patent Application Publication No. WO 2016/130905 A1), filed on Feb. 12, 2016, which claims benefit of U.S. Patent Application No. 62/115,851, filed on Feb. 13, 2015, the disclosures of which are hereby incorporated by reference herein in their entireties.

BACKGROUND OF THE INVENTION

Historically, partitioning of biomarkers from blood to sweat has been demonstrated in great detail. As more of these biomarkers emerge, sweat appears to be a convincing media for continuous and spontaneous health monitoring. However, 'clinical' techniques of sample collection, purification and analysis have restricted growth in the sweat-sensing area because of the cost and time associated with these techniques. With the advent of miniaturized sensors, however, many of these issues can be alleviated. Still, a large task has largely been left unexplored for compact sweat sensing technologies: sample extraction and collection.

Common techniques for sweat stimulation and analysis involve sweat stimulation in a region from a sweat generating unit 10, followed by removal of this unit 10 from the skin 12, cleaning of the skin 12 and reapplication of a sensing unit 14 or collection device 16, as shown in FIGS. 1A-1C. Often, the sensing unit 14 has integrated communication protocol to alert the user. This communication method could be via wireless or wired connections. For example, cystic fibrosis testing often involves this technique as demonstrated by ELITechGroup® in their Macroduct® and Nanoduct® products. This technique is problematic because it requires a two-step process that is inconvenient, non-continuous, and where reproducibility could be difficult.

Further, contamination from the stimulation reservoir and sensor region is unavoidable as they share the same area. In reference to FIGS. 1A-1C, the sweat generation unit 10 has potential to alter the state of the skin 12, whether that includes excessive hydration, thermal heating, irritation, pharmacological side-effects, or another side effect. This adds a confounding factor to sensing sweat analytes when the sensing unit 14 or collection device 16 is placed on the skin.

Attempts to reduce contamination have previously been made. For example, a technique includes utilizing an isolating membrane between sweat stimulation mechanisms and the sensors and sensing sites. However, such techniques utilizing isolating membranes (or similar techniques) may only partially or temporarily separate sweat stimulation mechanisms, such as an electric field and/or chemicals, from the sensors and sensing sites. In the instance of isolating membranes, these also have the drawback of increasing the dead volume between a sensor and the skin 12, which reduces temporal resolution. Furthermore, horizontal iontophoretic driving of an iontophoretic chemical, such as pilocarpine, may be used. However, this will again subject the sensor, sweat, and skin to an electric field and/or contamination. For many biomarkers and sensors, such interference could reduce performance of a sweat sensing device, in some cases making sensing impossible. There is an increasing need to provide improved sweat sensing techniques and devices that address one or more of the above drawbacks.

SUMMARY OF THE INVENTION

Embodiments of the present invention rely in part on the premise that sudomotor axon reflex (SAR) sweating can be utilized by a sweat inducing and sensing device for sweat analysis. SAR sweating can potentially be initiated by a variety of mechanisms: thermal, direct-electrical, chemical, occlusion, and others. In this setting, direct-electrical refers to a biophysical phenomenon where sweating is initiated by the flow of electron and ion current without the aid of a chemical active compound. Additionally, embodiments of the present invention can greatly reduce contamination and improve chronological sampling of sweat. Furthermore, the embodiments of the present invention described below have the ability to use a variety of sensing techniques which greatly improves the impact and variety of applications for such a device.

BRIEF DESCRIPTION OF THE DRAWINGS

The objects and advantages of the present invention will be further appreciated in light of the following detailed descriptions and drawings in which.

DETAILED DESCRIPTION OF THE INVENTION

The embodiments of the present invention described herein improve greatly on prior simultaneous stimulation and collection of sweat sample methods, such as that presented in FIG. 1.

Embodiments of the present invention take advantage of a biological response referred to as the sudomotor axon reflex ("SAR"). This mechanism acts on the premise that innervation of sweat glands occurs as a result of peripheral functionality of sudomotor units (i.e., the body will stimulate a series of sweat glands directly underneath the stimulation region, "direct stimulation", but will also generate sweat from sweat glands outside of this region, "indirect stimulation"). For example, in the case of chemical sweat stimulation, the sweat stimulant acts on the neural receptors surrounding the sweat glands to elicit a sweating response. The chemical stimulant can act on two primary receptors at the base of the sweat gland: muscarinic or nicotinic receptors. SAR response is typically observed with chemicals that interact strongly with nicotinic receptors at the base of the sweat gland. For example, pilocarpine acts weakly on nicotinic receptors and is therefore a poor chemical stimulant for SAR response. However, nicotine acts strongly on nicotinic receptors and is therefore an attractive stimulant for SAR response. Furthermore, there are chemical stimulants, such as acetylcholine, that act strongly on both muscarinic and nicotinic receptors, which can be leveraged to produce a SAR response. It should be recognized that, although not named, multiple other chemical stimulants are capable of causing a SAR response and are useful in embodiments of the present invention. Although there has largely been limited research in this area of sweat stimulation, it is also hypothesized that thermal, direct-electrical, occlusion, and other sweat stimulant techniques will produce a similar antidromic responses as chemical stimulants. Consequently, one can stimulate sweat glands in a region within close proximity of a sensor array to generate sweat directly underneath the stimulation region ("direct stimulation") and directly underneath the sensors ("indirect stimulation"). Typically, the "spreading" of SAR induced sweating, the distance from the edge of direct stimulation to the decay of indirect stimulation, is limited on the order of several tens of millimeters (e.g., up to about 30 mm). The degree of a SAR response, in the case of chemical stimulation, depends largely on the amount and type of sweat stimulant which is delivered to a given location.

Figure 2:
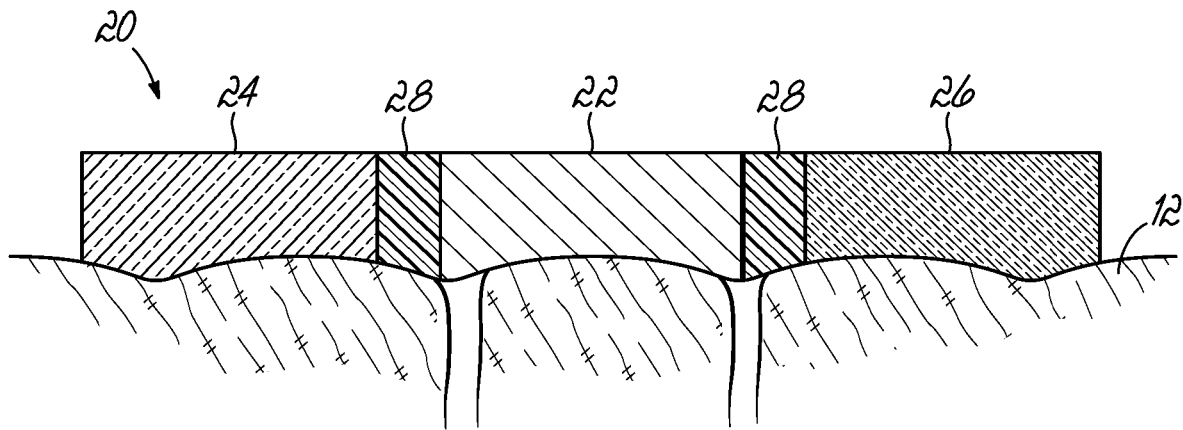
FIG. 2 is a cross-sectional view of a device according to an embodiment of the present invention showing separate sensing and collection units.

In reference to FIG. 2, a device 20 according to an embodiment of the present invention may have a structure with a sweat generation unit 22 and at least one of two analysis units: a collection unit 24 and a sensing unit 26. The sweat generation unit 22 is capable of directly initiating sweat in a direct stimulation region and initiating SAR sweating in indirect stimulation regions under the collection unit 24 and the sensing unit 26. In one embodiment, the sweat generation unit 22 includes a chemical stimulant, such as acetylcholine, methacholine, nicotine, carbachol, or another chemical that is capable of initiating SAR sweat. The collection unit 24 and the sensing unit 26 are located separately from the sweat generation unit 22 along the skin 12. In one embodiment, the analysis units may be spaced apart from the direct stimulation region by a distance of about 0.1 mm to about 30 mm. The SAR-initiated sweat is then collected and sensed by the collection unit 24 and the sensing unit 26, respectively. As shown, embodiments of the present invention promote a single-step process, which is an advantage over previous devices where sweat generation and sweat analysis were performed in multiple steps. Further, continuous and multiple occurrence SAR-initiated sweating for the purpose of sweat analysis is possible. For example, sweat may be sensed or collected in one instance in time, continuously for a length of time, or a combination thereof.

Optionally, each of these regions (sweat generation, sweat sensing, and sweat collecting) may be separated by an isolation layer 28 as shown in FIG. 2. This isolation layer 28 could take many forms or materials such as an adhesive or rubber with the purpose of electrically and/or fluidically isolating regions of the device. The isolation layer 28 serves to improve the reliability of the device and helps assure that fluid will not mix between regions or create unwanted electrical connections (e.g., "electrical shorts"). Furthermore, since this isolation layer 28 is preferably water-insoluble, common adhesives will not only provide electric and fluidic isolation but will also aid in keeping the device on the skin 12. Furthermore, in some cases, the isolation layer 28 protects the sensing unit 26 from voltages or currents applied to the sweat generation unit 22.

The term "sweat generation unit", including other denotative or connotative phrases, as used herein, captures a plurality of sweat stimulation methods that are capable of initiating SAR sweating. For example, a sweat generation unit may involve one or more of chemical, thermal, direct-electrical, or other suitable mechanisms which stimulates the generation of sweat and are not specifically described. The most common technique for sweat stimulation is a chemical technique referred to as iontophoresis. This involves electric-field driven movement of a sweat stimulant drug into the skin surface, ultimately reaching the secretory coil of the sweat gland, to initiate sweating. It should be recognized that, although iontophoresis is the most common chemical technique, electroporation, injection or microneedles delivery, passive diffusion of a sweat stimulant from a drug reservoir, which may be improved by a diffusion enhancer (e.g., propylene glycol) applied to the skin prior to device application or incorporated directly into the stimulation unit itself, or other techniques are also possible routes of chemical delivery of a sweat stimulant in embodiments of the present invention. Utilizing such a design according to the present invention will greatly reduce contamination between a stimulation reservoir (e.g., in the sweat generation unit 22) and collection and/or the sensor region (e.g., relating to the collection unit 24 and the sensing unit 26).

Additionally, the terms "sensing unit" and "sensing mechanism," including other denotative or connotative phrases, as used herein could include one or more of a plurality of mechanisms for sensing sweat and/or its components or properties including potentiometric, amperometric, conductometric, impedance spectroscopy, skin impedance, galvanic skin response (GSR), or other suitable mechanisms. Similarly, the term "collection unit", including other denotative or connotative phrases, as used herein, describes a collection method, material, or structure.

The terms "collection and/or sensing unit" and "analysis unit", including other denotative or connotative phrases, as used herein, describe a unit that is capable of sensing sweat, collecting sweat, or a combination of the two. A sensing unit (e.g., sensing unit 26) and/or a collection unit (e.g., collection unit 24) may have integrated electronics or controls which monitor physiological parameters, provide feedback to a user or similar function. In an embodiment with both a sensing unit(s) and a collection unit(s) (e.g., device 20), the units may function independently of each other or may operate together.

Sweat generation units, collection units, sensing units, and combinations of such units may include a variety of functional aspects such as wired or wireless communications, rigid or flexible structure or other method, material, function, or particular structure not specifically described here. These units may also have intelligent communication between or within each unit via optical, electrical, or similar communication method (not shown).

Figure 3:
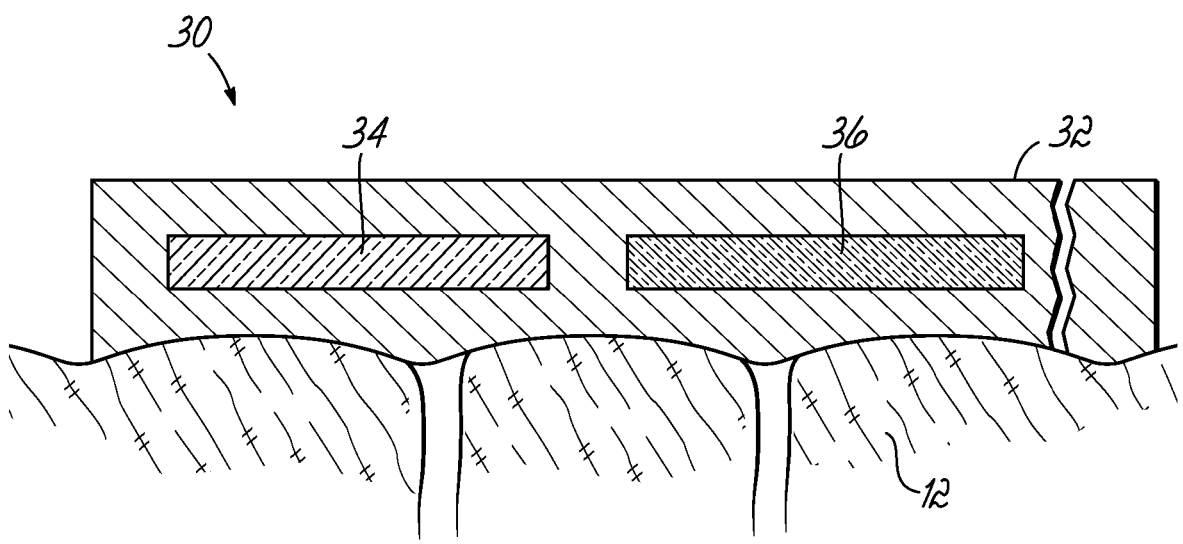
FIG. 3 is a cross-sectional view of a device according to another embodiment of the present invention showing the sensing and collection units embedded within the sweat generation unit.

In another embodiment, FIG. 3 shows a device 30 where a sweat generation unit 32 is placed in vertical alignment with a collection unit 34 and a sensing unit 36. Although the collection 34 and/or sensing unit 36 are shown being located within the sweat generation unit 32, another embodiment may include at least one collection 34 and/or sensing unit 36 located directly on skin 12 with the sweat generation unit 32 placed directly over said components (not shown). Although a minimal amount of direct sweating may possibly be produced underneath the collection unit 34 or sensing unit 36 from the sweat generation unit 32, indirect (SAR) sweating may be the only suitable mechanism for generating sufficient sweat to sense and/or collect. For example, in the case of chemical stimulation via iontophoresis, the collection unit 34 and the sensing unit 36 reduce the effectiveness for direct stimulation directly underneath these units. Essentially, these units block or alter the effectiveness of a stimulation technique that initiates non-SAR sweating. However, in leveraging SAR stimulation, the device 30 will overcome these limitations by indirectly generating sweat underneath the units 34, 36. In other words, to generate sufficient sweat under the collection unit 34 and the sensing unit 36, the sweat generation unit 32 includes a mechanism for initiating SAR sweating.

The construction of device 30 could simplify device construction and assembly compared to other configurations. For example, in one embodiment, units 34, 36 could be fabricated using standard flexible electronics techniques (such as on PET or Kapton film), and pressed against skin 12. The sweat generation unit 32 could be a gel including a sweat stimulant and a driving electrode (not shown) that is pressed down against units 34, 36 and skin 12. Some of the iontophoretic chemical stimulant in sweat generation unit 32 may find itself between units 34 and 36 and skin (similar to as diagramed in FIG. 3), but would be incapable of generating a strong direct stimulation of sweat, and thus this example embodiment would rely on the indirect stimulation of sweat by SAR to cause sweat to be received by units 34, 36.

A benefit of the vertical alignment between the analysis units (e.g. collection unit 34 and sensing unit 36) and a sweat generation unit (e.g., sweat generation unit 32) is an increase in the density of the units. This benefit could be realized in other configurations of the sweat generation and analysis units, such as in the honeycomb formation described below. Depending on the sweat generation mechanism, SAR-initiated sweat may only be able to be collected or sensed up to several millimeters away from the direct stimulation region. Therefore, embodiments of the present invention achieve a greater benefit with a high density of sweat generation and analysis units.

Figure 4A:
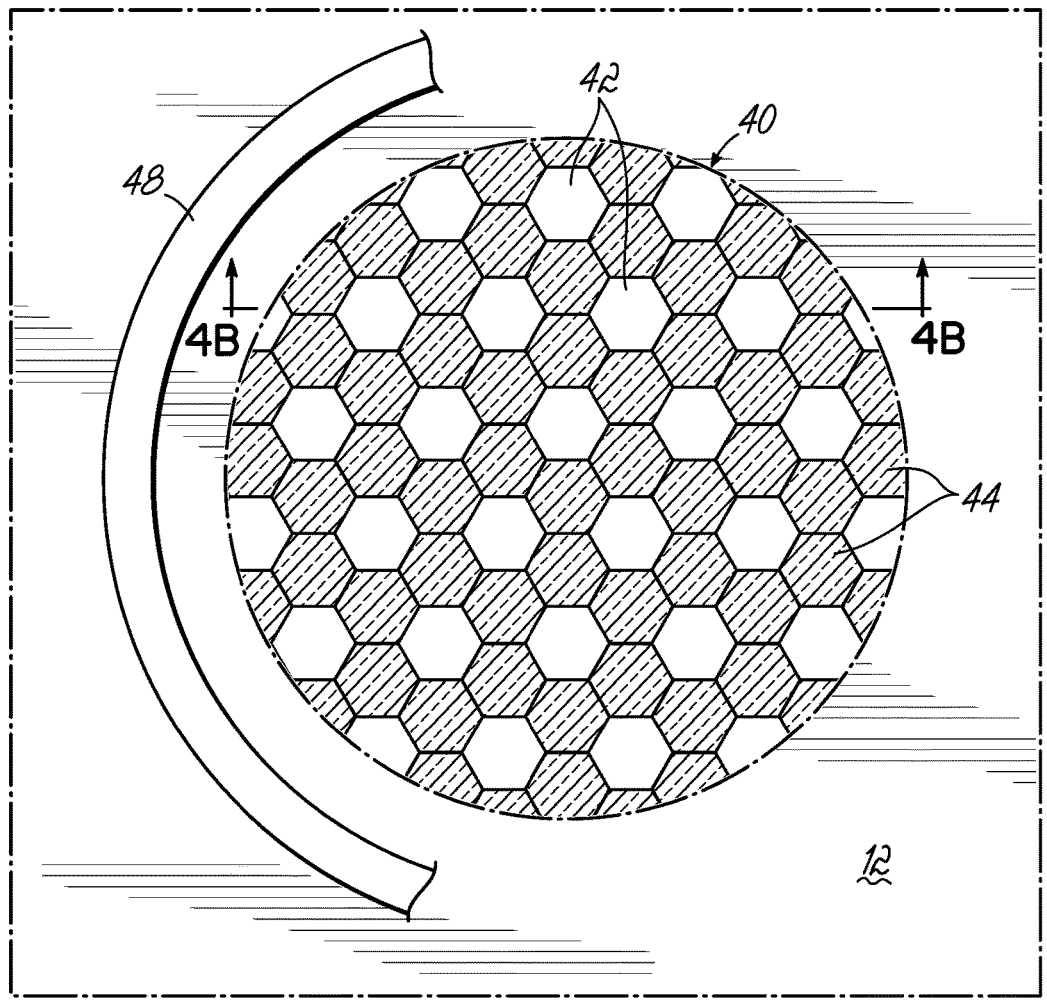
FIG. 4A is a top view of a device according to another embodiment of the present invention showing a hexagonal arrangement.
Figure 4B:
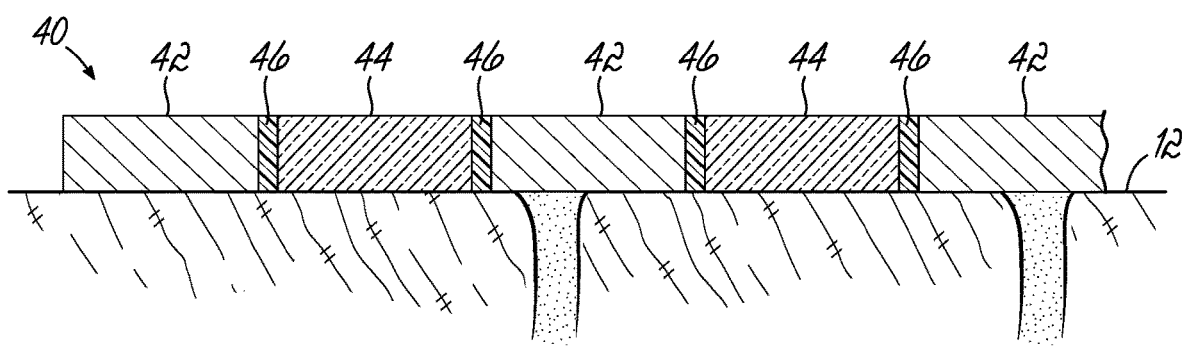
FIG. 4B is a cross-sectional view of the device of FIG. 4A.

Regarding FIGS. 4A and 4B, in one embodiment, a device 40 is shown positioned on the skin 12. The device 40 includes a plurality of sweat generation units 42 and a plurality of collection and/or sensing units 44 arranged in a honeycomb structure. In one embodiment, the sweat generation units 42 are iontophoretic in nature and the collection and/or sensing units 44 include potentiometric sensors. In this configuration, the collection and/or sensing units 44 are placed spatially so that each unit 44 is within close proximity of a sweat generation unit 42 (i.e., the units 44 are located above indirect stimulation regions). With the hexagonal arrangement of device 40, each sensing unit 44 is surrounded by three sweat generation units 42, increasing the probability for a SAR sweating response underneath the sensing units 44. The device 40 further includes an optional isolation material 46 (best shown in FIG. 4B) that isolates the collection and/or sensing units 44 from the sweat generation units 42, which improves the device integrity and functionality. This isolation material 46 could take one of many forms and materials as previously described. Those of ordinary skill in the art will recognize that the structure may be configured to be a similar shape other than a hexagonal or a honeycomb structure. As shown in FIG. 4A, the stimulation source (i.e., the sweat generation units 42) and the collection and/or sensing units 44 are separate in horizontal location on skin, with no horizontal overlap. The present invention also contemplates devices where at least partial overlap exists where the benefit of SAR sweating in the present invention is still realized, such as device 30 presented in FIG. 3.

Furthermore, in a device according to the present invention where the sweat generation method is via direct-electrical methods or iontophoresis, a return electrode can be placed on the periphery of the device so as to maximize the amount of current or drug delivered in the desired location. For example, in FIG. 4A, a return electrode 48 is positioned around an edge of the device 40.

Figure 5:
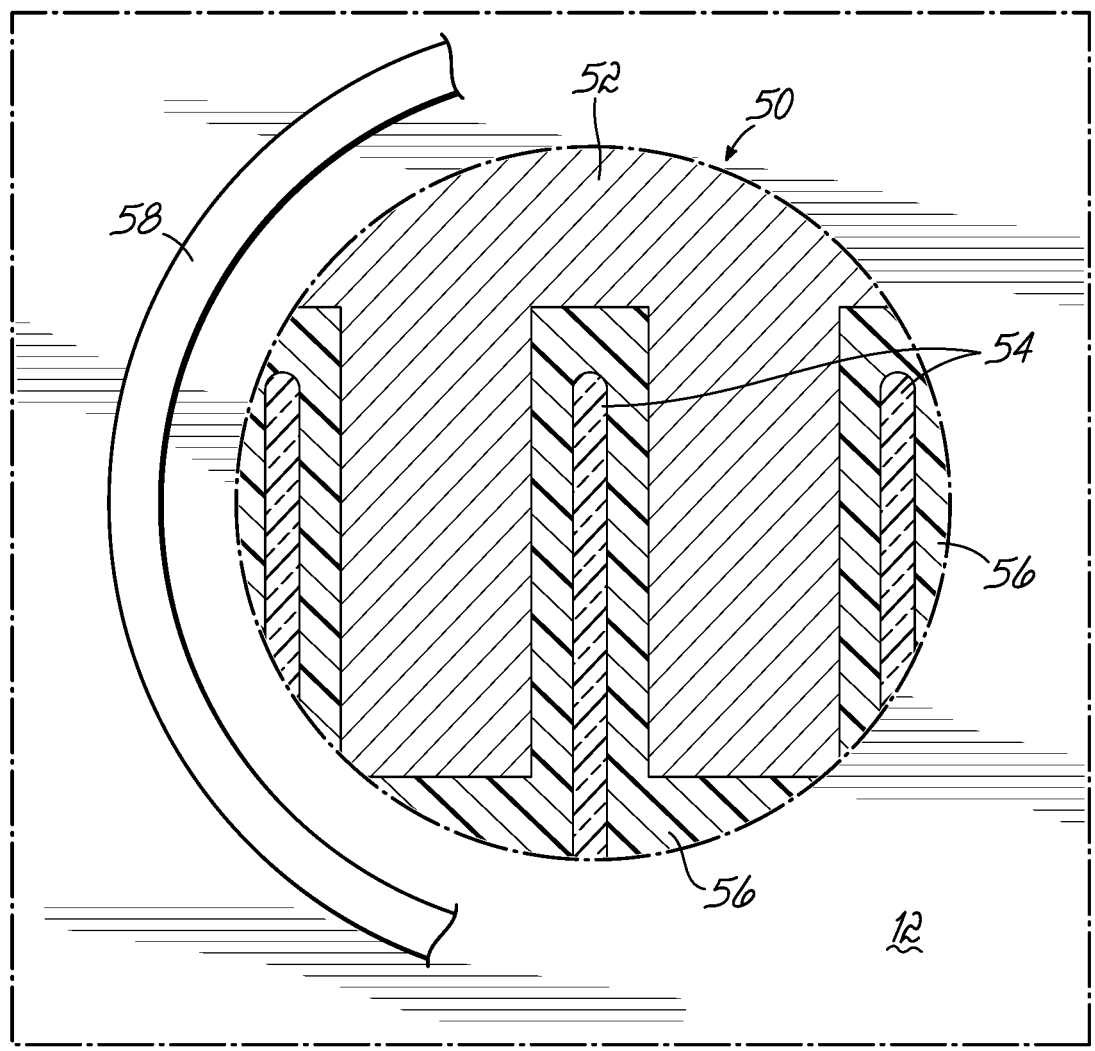
FIG. 5 is a top view of a device according to another embodiment of the present invention showing a high aspect ratio arrangement.

In FIG. 5, a portion of a device 50 according to an embodiment of the present invention is shown. The device 50 includes a single large area or a plurality of sweat generation units 52, a plurality of collection and/or sensing units 54, and an optional isolation material 56. The structure utilizes a greater than unity aspect ratio of sensors and/or collection units 54, which minimizes the amount of lateral distance required to leverage SAR sweating. Due to the need to be above at least one active sweat gland, and/or due to signal to noise requirements, some collection and or sensing units must have a minimum total area of contact with skin. A greater than unity aspect ratio allows a minimum area to be achieved, while further minimizing the amount of lateral distance required to leverage SAR sweating. In one embodiment, the length/width aspect ratio may be about 2:1 or, alternatively, about 1:2. Although FIG. 5 shows a rectangular configuration, those of ordinary skill in the art will recognize that a rectangular configuration is not required and a similarly intended effect can be achieved via a concentric design or similar structure (not shown). For example, other geometries, such as a star shape, may also be included that feature a greater than unity aspect ratio. Where the sweat generation method for the device 50 is via direct-electrical methods or iontophoresis, a return electrode 58 can be placed on the periphery of the device 50 so as to maximize the amount of current or drug delivered in the desired location.

Figure 6A:
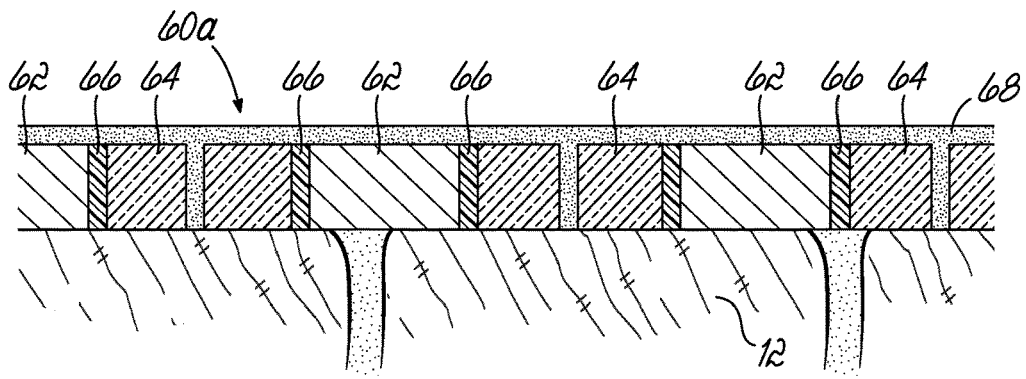
FIGS. 6A and 6B are cross-sectional views of devices according to embodiments of the present invention showing a fluid management system in differing arrangements.
Figure 6B:
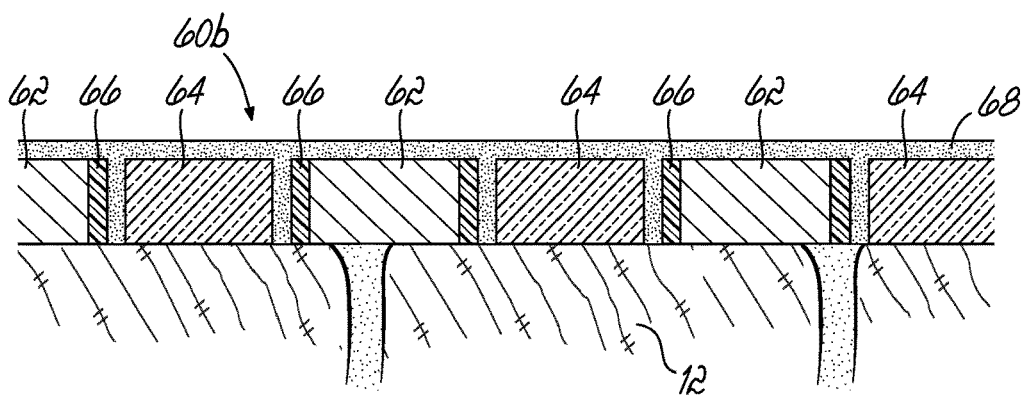
Figure 6C:
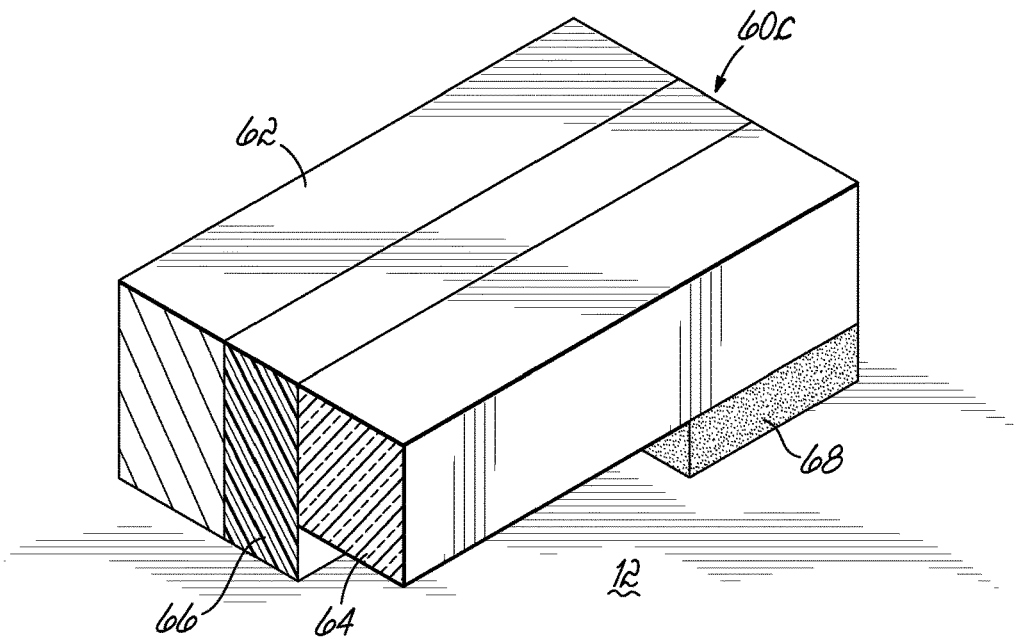
FIGS. 6C and 6D are perspective views of devices according to embodiments of the present invention showing a fluid management system in differing arrangements.
Figure 6D:
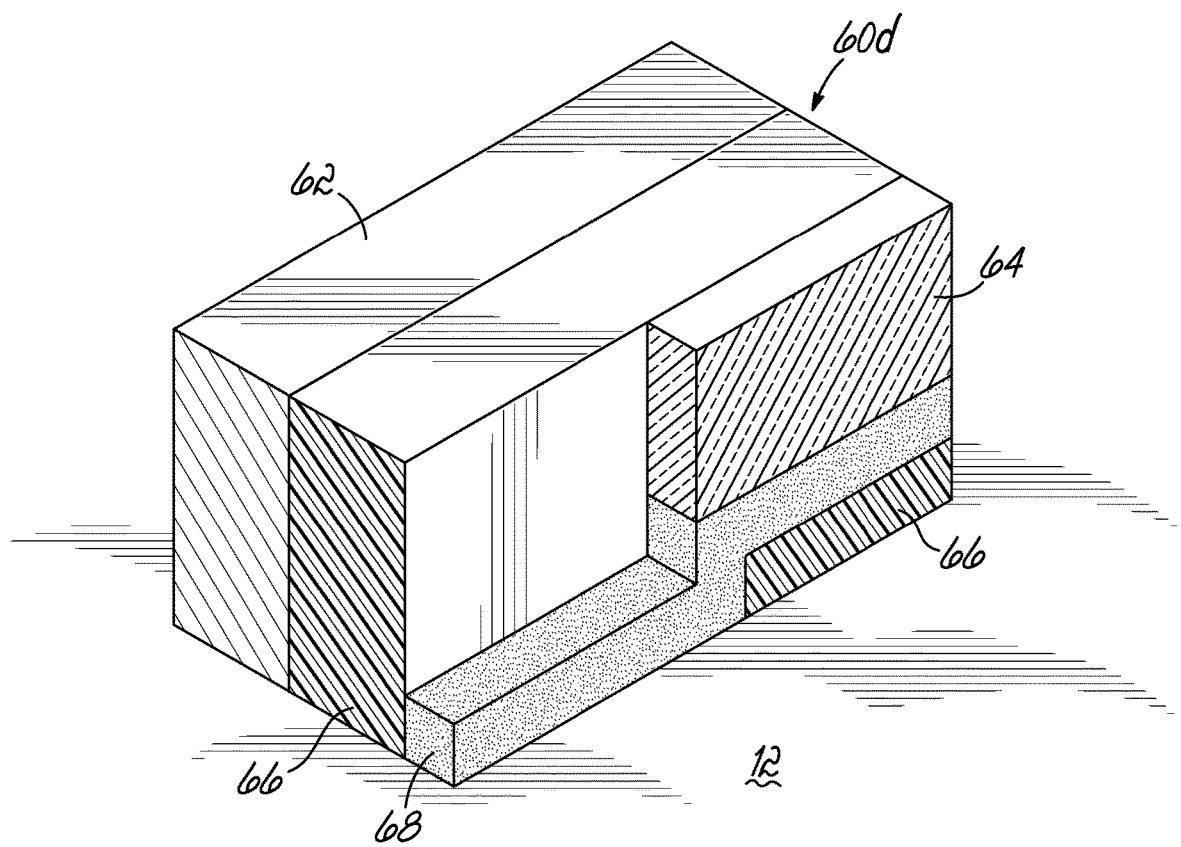

With reference to FIGS. 6A-6D, devices according to various embodiments are shown that include improved sweat fluid management. More particularly, devices 60a, 60b, 60c, and 60d are shown including sweat generation unit(s) 62, collection and/or sensing unit(s) 64, and isolation materials 66. An optional wicking material 68 is used as an additional component that acts as a fluid management feature, which improves performance. The wicking material 68 may also be used to bring sweat from skin 12 to a collection and/or sensing unit 64, as described below. A device including the wicking material 68 may have varying configurations. In one embodiment, the wicking material 68 may act to actively move previously analyzed sweat sample to a disposal region (not shown) thereby increasing effective sweat sampling time resolution. For example, the wicking material 68 may be included as a through-hole component in the collection and/or sensing unit 64 (FIG. 6A), at the edge of the collection and/or sensing unit 64 (FIG. 6B), or in the plane of the collection and/or sensing unit 64 (FIG. 6C). Further, this wicking material 68 or similar microfluidic structure could be used to transport sweat from the skin to the collection and/or sensing unit(s) 64 (specifically shown in FIG. 6D). For ease of fabrication or intended application, one particular structure may be more beneficial than another.

For instance, regarding device 60a, there may be benefit in wicking sweat to a central location within the collection and/or sensing unit 64 to reduce likelihood of fluid buildup near the isolation boundary 66. Similarly, in device 60c, the wicking material 68 is shown partially extended along the length of the sensor and/or collection unit 64, which may prove beneficial where a small volume of sweat is generated underneath the sensor and/or collection unit 64 before being wicked away. In this instance, the wicking material 68 acts as a static, volume-limiting pump. Furthermore, a combination of one of the structures described may prove beneficial. In an exemplary embodiment, the wicking material 68 may be paper or a polymer or microfluidic feature that operates via capillary action. Further, the wicking material 68 could be segmented utilizing more than one wicking material, such as a combination of paper and polymer or another combination of similar wicking materials.

Prediction of Typical Parameters

Peripheral (indirect) sweating after 5 minutes of iontophoresis is significant (e.g., sweat rates of about 1-3 nL/min/gl) on average to at least 8 mm from the boundary of the direct stimulation region. A sweat stimulant could be delivered iontophoretically or by another method and could constitute a wide range of various sweat stimulants (e.g., pilocarpine, acetylcholine, etc.). Considering that sensors can be fabricated utilizing previously demonstrated technology well below 8 mm in diameter (e.g., 500 µm in diameter), an array of biomarker sensors may be easily placed within the indirect sweating region. Although indirect sweating results in a reduction in sweat rate (e.g., about 60% reduction as compared to the sweat rate in the area being directly stimulated), the reduction of the risk of contamination and potential to reduce drug dosage (as described below) outweigh this downfall.

The spacing between the stimulation regions and the collection and/or sensor units may vary depending on the configuration. In one embodiment, an array of stimulation units and analysis units may have a minimum half-pitch (smallest repeating unit) less than one millimeter at an accuracy within tens of micrometers or better.

Sweat Stimulation—Sampling Effectiveness

Figure 1A:
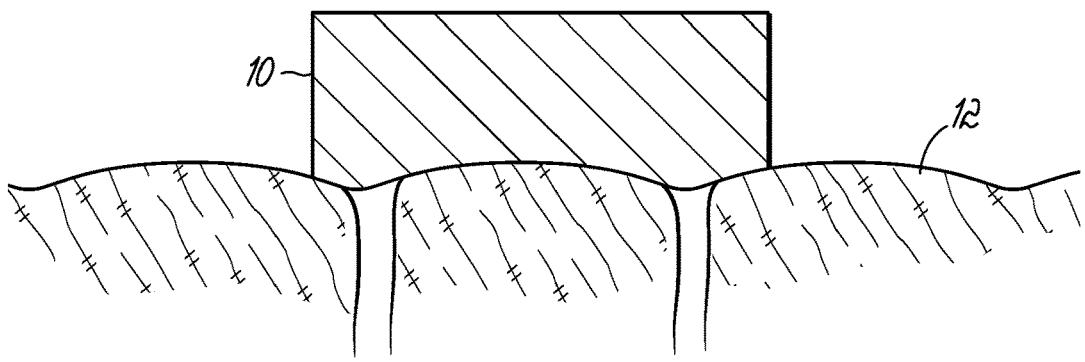
FIGS. 1A-1C are cross-sectional views of a prior art sweat stimulation, sensing, and collection technique.
Figure 1B:
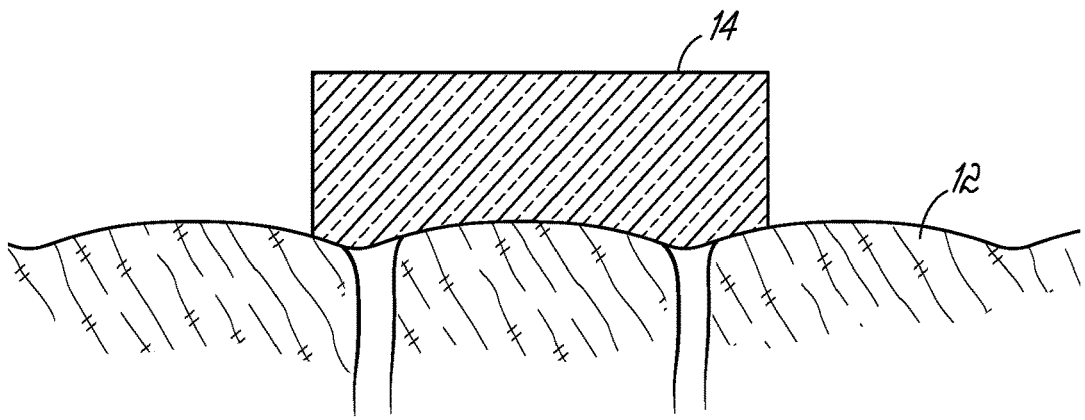
Figure 1C:
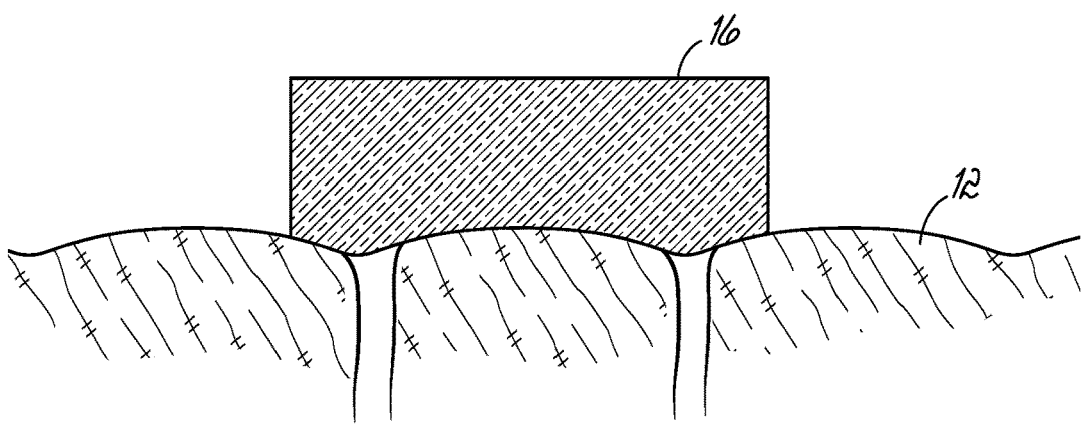

A sampling effectiveness metric ("SE") for comparing sweat stimulation devices can be defined by Equation 1:

$$SE = \frac{Q}{\Gamma}$$

where Q is the sweat rate per minute, and $\Gamma$ is the dose of drug stimulant delivered in the case of iontophoretic delivery. A base metric, e.g., $SE_0$, for the case of the stimulation region being the same as the collection region (e.g., as shown in FIGS. 1A-1C) may be used to compare sweat stimulation devices without using actual sweat rate data. The hexagonal device 40 shown in FIGS. 4A and 4B have one stimulation unit 42 per four total stimulation and collection/sensor units 42, 44 per unit cell and would utilize at least ¼, or 25%, of the stimulation region and, thus, 25% of the dosage $\Gamma_0$. Similarly, the sensing/collection regions would comprise 75% of the original area, $A_0$. Further, as described above, the hexagonal device 40 would generate 40% of the original sweat rate, $Q_0$, in the indirect regions. Therefore, in comparison to the case of the same stimulation and collection region, a hexagonal array would provide a decrease in total sweat rate of 70% (i.e., 100%−(40% $Q_0$*75% $A_0$)=70%), resulting in a sweat rate of 30% of the original sweat rate, $Q_0$, while using 25% of the original dose, $\Gamma_0$. This calculation completely excludes any sweat generated underneath the stimulation region. Overall however, the SE ratio would increase 20% as a result of the reduced stimulation area (i.e., 0.30 $Q_0$/0.25 $\Gamma_0$=1.2 $SE_0$). Further, if one is able to collect the sweat generated underneath the stimulation region, the SE could increase 120% (i.e., (0.30 $Q_0$+0.25 $Q_0$)/0.25 $\Gamma_0$=2.2 $SE_0$). Thus, not only is the contamination reduced with this method, but the sampling efficiency (SE) is increased. It should be noted that this reduction in area and 'dose' applies to all methods of stimulation where these nerve fibers are activated. Therefore, thermal, direct-electrical or other methods would also benefit from this unique device structure.

In alternative embodiments, the stimulation region could be much smaller than the collection/sensor region. This is because only a small area would be required to initiate the SAR response of many nearby sweat glands. Furthermore, in the case of iontophoresis, this reduction in the stimulation area would improve the SE, which would allow for less drug delivery (dosage) to achieve the same previously attained SE.

Dead Volume

A metric for comparing the dead volume ("DV") of such devices can be defined by Equation 2:

$$DV = \frac{V_{dead}}{A_{sensor}}$$

where $V_{dead}$ is the dead volume between the sensor and skin, and $A_{sensor}$ is the area of the sensor. Comparing to an instance where the stimulation and collection regions are in the same area and the device includes an element to reduce contamination (not shown), such as a membrane, the gap between the sensor and skin could be on the order of 200 µm (e.g., due to roughness of skin, thickness of paper wicking layer, thickness of a drug reservoir, etc.). However, with indirect stimulation, one can greatly improve the contact between the skin and sensor while reducing the contamination from the stimulation. In this regard, the device may be so intimate with the skin that the only source of dead volume would be from the topology of the skin (e.g., about 30 µm). Thus, the reduction in dead volume between the device where the stimulation and collection regions are in the same area and this embodiment would be a reduction of at least 6× (200 µm/30 µm). This holds great significance when one estimates the time to "refresh" the sweat underneath the sensor. If there is 6× less volume to refill underneath the sensor, then for a given flow rate, the time required to refresh the sweat underneath the sensor would also be reduced 6×. This has profound impact on time-resolution capabilities.

Total Figure of Merit (TOT-FOM)

Utilizing the two calculations above for SE and DV and assuming the addition of an isolating membrane between sensor and skin, the effective improvement may be the multiplication of these two values. Therefore, the total improvement between an exemplary previous device described above and an embodiment of the present invention would be an improvement of at least 7.2× with potentially an improvement approaching 13.2×—when sweat rate per unit area, dose per unit area and dead volume per unit area are considered.

While all of the invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicants' general inventive concept.

What is claimed is:

1. A wearable sweat sensing device, comprising:
    a sweat stimulator configured to be placed on a surface of a first region of a device wearer's skin to directly stimulate sweating in the first region and to indirectly stimulate sweating in a second region of the wearer's skin, wherein the second region is distinct from the first region;
    a sweat analyzer configured to be placed on a surface of the second region of the device wearer's skin, the sweat analyzer configured to collect a sweat sample from the second region, and to measure one or more analytes in the sweat sample; and
    an isolation layer positioned to fluidically isolate the sweat stimulator from the sweat analyzer.

2. The device of claim 1, wherein the sweat stimulator is configured to have a minimum area in contact with the device wearer's skin, a first dimension, and a second dimension, and wherein the ratio of the first dimension to the second dimension is one or more of the following: greater than 1 to 1, 2 to 1, or greater than 2 to 1.

3. The device of claim 1, wherein the sweat stimulator is configured to have a surface area in contact with the device wearer's skin, and a minimum volume relative to the surface area.

4. The device of claim 1, wherein the sweat stimulator is configured to use a pair of iontophoresis electrodes to drive a sweat stimulant into the first region.

5. The device of claim 4, wherein a return electrode is located on a periphery of the device.

6. The device of claim 4, wherein the sweat stimulant comprises a chemical stimulant selected from a group consisting of acetylcholine, methacholine, nicotine, and carbachol.

7. The device of claim 1, wherein the sweat stimulator is electrically isolated from the sweat analyzer.

8. The device of claim 1, wherein the sweat analyzer further comprises a collector configured to collect and convey the sweat sample from the second region to the sweat analyzer.

9. The device of claim 8, wherein the collector further comprises a wicking material.

10. The device of claim 1, wherein the first region is separated from the second region by a distance of 0.1 mm to 30 mm.

11. The device of claim 1, further comprising a plurality of sweat stimulators and one or more sweat analyzers, and wherein the plurality of sweat stimulators and the one or more sweat analyzers are spatially arranged to increase the probability of a SAR sweating response underneath the one or more sweat analyzers.

12. The device of claim 1, further comprising a plurality of sweat stimulators and a plurality of sweat analyzers, and wherein the plurality of sweat stimulators and the plurality of sweat analyzers are arranged spatially in a hexagonal pattern.

13. The device of claim 11, wherein the plurality of sweat stimulators and the one or more sweat analyzers are arranged in a concentric pattern.

* * * * *